(12) United States Patent
Carls et al.

(10) Patent No.: US 9,770,338 B2
(45) Date of Patent: Sep. 26, 2017

(54) POSTERIOR TOTAL JOINT REPLACEMENT

(71) Applicant: HH Spinal LLC, Chattanooga, TN (US)

(72) Inventors: Thomas Carls, Memphis, TN (US); Eric C. Lange, Collierville, TN (US); Danny Braddock, Jr., GermanTown, TN (US); Steven C. Humphreys, Chattanooga, TN (US); Scott D Hodges, Ooltewah, TN (US); Richard G Fessler, Winnetka, IL (US); Jeffrey Zhang, Collierville, TN (US)

(73) Assignee: HH SPINAL LLC, Chattanooga, TN (US)

( * ) Notice: Subject to any disclaimer, the term of this patent is extended or adjusted under 35 U.S.C. 154(b) by 296 days.

(21) Appl. No.: 14/486,065

(22) Filed: Sep. 15, 2014

(65) Prior Publication Data
US 2015/0005884 A1 Jan. 1, 2015

Related U.S. Application Data

(60) Division of application No. 11/839,821, filed on Aug. 16, 2007, now Pat. No. 8,864,832, and a continuation
(Continued)

(51) Int. Cl.
*A61F 2/44* (2006.01)
*A61B 17/70* (2006.01)
*A61F 2/30* (2006.01)

(52) U.S. Cl.
CPC ............ *A61F 2/442* (2013.01); *A61F 2/4405* (2013.01); *A61F 2/4425* (2013.01);
(Continued)

(58) Field of Classification Search
CPC ...... A61F 2/442; A61F 2/4405; A61F 2/4425; A61F 2002/30563; A61F 2002/30578;
(Continued)

(56) References Cited

U.S. PATENT DOCUMENTS 6,679,915 B1 * 1/2004 Cauthen ................ A61F 2/4425
623/17.11
7,811,326 B2 * 10/2010 Braddock, Jr. ........ A61F 2/4405
623/17.14
(Continued)

FOREIGN PATENT DOCUMENTS

| CN | 1713866 A | 12/2005 |
|---|---|---|
| CN | 1976651 A | 6/2007 |
| WO | 2008151115 A2 | 12/2008 |

*Primary Examiner* — Ellen C Hammond
(74) *Attorney, Agent, or Firm* — Brainspark Associates, LLC

(57) ABSTRACT

A prosthetic system for implantation between upper and lower vertebrae comprises an upper joint component. The upper joint component comprises an upper contact surface and an upper articulation surface. The system further includes a lower joint component. The lower joint component comprises a lower contact surface and a lower articulation surface configured to movably engage the upper articulation surface to form an articulating joint. The articulating joint is adapted for implantation within a disc space between the upper and lower vertebrae, allowing the upper and lower vertebrae to move relative to one another. The system further includes a bridge component extending posteriorly from one of either the upper or lower joint components and from the disc space. The bridge component has a distal end opposite the one of the either upper or lower joint components. The distal end of the bridge component comprises a connection component adapted to receive a fastener.

7 Claims, 12 Drawing Sheets

Related U.S. Application Data of application No. 11/757,084, filed on Jun. 20, 2007, now abandoned.

(52) U.S. Cl.
CPC . *A61B 17/7001* (2013.01); *A61F 2002/30331* (2013.01); *A61F 2002/30563* (2013.01); *A61F 2002/30578* (2013.01); *A61F 2002/30624* (2013.01); *A61F 2002/30652* (2013.01); *A61F 2002/30654* (2013.01); *A61F 2002/30662* (2013.01); *A61F 2002/30884* (2013.01); *A61F 2002/448* (2013.01); *A61F 2220/0033* (2013.01); *A61F 2250/0004* (2013.01); *A61F 2310/00796* (2013.01); *A61F 2310/00976* (2013.01)

(58) Field of Classification Search
CPC .. A61F 2002/30624; A61F 2002/30652; A61F 2002/30662; A61F 2002/30884; A61F 2002/448; A61F 2220/0033; A61F 2002/30331

See application file for complete search history.

(56) References Cited

U.S. PATENT DOCUMENTS

| | | | |
|---|---|---|---|
| 2003/0208273 A1* | 11/2003 | Eisermann | A61F 2/4425 623/17.14 |
| 2003/0233146 A1* | 12/2003 | Grinberg | A61F 2/4425 623/17.14 |
| 2004/0073311 A1* | 4/2004 | Ferree | A61F 2/442 623/17.14 |
| 2004/0186570 A1* | 9/2004 | Rapp | A61F 2/4455 623/17.11 |
| 2005/0154461 A1 | 7/2005 | Humphreys et al. | |
| 2005/0154464 A1* | 7/2005 | Humphreys | A61F 2/4405 623/17.16 |
| 2005/0154466 A1* | 7/2005 | Humphreys | A61B 17/7022 623/17.16 |
| 2005/0165407 A1 | 7/2005 | Diaz et al. | |
| 2005/0171610 A1* | 8/2005 | Humphreys | A61F 2/4405 623/17.15 |
| 2006/0241769 A1* | 10/2006 | Gordon | A61B 17/7005 623/17.13 |
| 2007/0073404 A1* | 3/2007 | Rashbaum | A61F 2/4425 623/17.14 |
| 2007/0173942 A1* | 7/2007 | Heinz | A61F 2/4425 623/17.15 |
| 2007/0179616 A1 | 8/2007 | Braddock et al. | |
| 2007/0191945 A1* | 8/2007 | Yu | A61F 2/4405 623/17.11 |
| 2007/0260317 A1* | 11/2007 | Ankney | A61B 17/1671 623/17.16 |
| 2008/0027547 A1* | 1/2008 | Yu | A61F 2/4405 623/17.13 |
| 2010/0298938 A1* | 11/2010 | Humphreys | A61F 2/4405 623/17.11 |

* cited by examiner

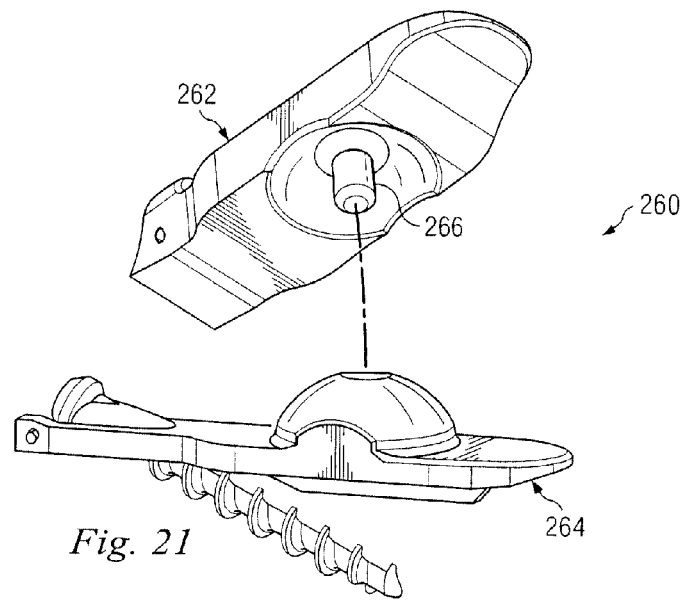
Fig. 21
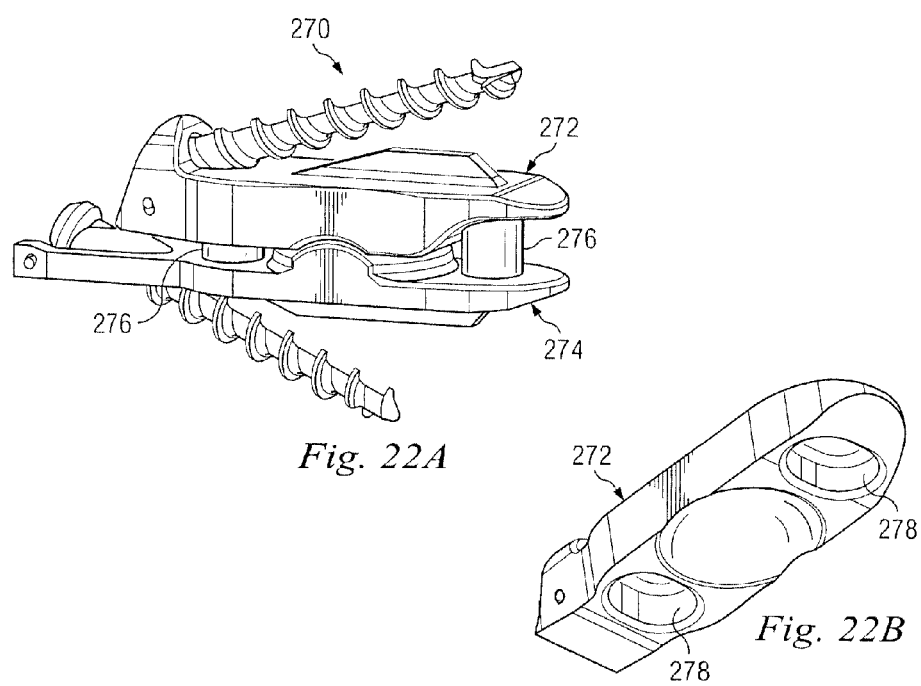
Fig. 22A
Fig. 22B

POSTERIOR TOTAL JOINT REPLACEMENT

CROSS REFERENCE TO RELATED APPLICATION(S)

This application is a divisional application of allowed U.S. patent application Ser. No. 11/839,821, filed Aug. 16, 2007, which is a continuation of U.S. patent application Ser. No. 11/757,084 filed Jun. 20, 2007.

CROSS-REFERENCE

This application is a continuation of, and claims priority to, U.S. application Ser. No. 11/757,084, filed on Jun. 1, 2007.

BACKGROUND

At times, the source of a patient's back pain may not be clear. Among possible causes for the pain are disease, degradation, or injury of the spinal disc or the associated facet joints. Spinal disc arthroplasty is one way of treating spinal joints to reduce pain while preserving motion within the joint. Alternative treatments focus on the facet joints, which may be removed and replaced with prosthetic devices. Currently, few options exist for treating the total spinal joint, including the spinal disc and the associated facet joints. Because of their size, existing disc arthroplasty devices often involve anterior surgical approaches. Besides being highly invasive, an anterior surgical approach does not allow the surgeon to easily access and repair or replace ailing facet joints. Therefore, a motion preserving joint replacement system is needed that treats the total spinal joint by replacing all or part of the function of both the spinal disc and the associated facet joints using less invasive procedures.

SUMMARY

In one embodiment, a prosthetic system for implantation between upper and lower vertebrae comprises an upper joint component. The upper joint component comprises an upper contact surface and an upper articulation surface. The system further includes a lower joint component. The lower joint component comprises a lower contact surface and a lower articulation surface configured to movably engage the upper articulation surface to form an articulating joint. The articulating joint is adapted for implantation within a disc space between the upper and lower vertebrae, allowing the upper and lower vertebrae to move relative to one another. The system further includes a bridge component extending posteriorly from one of either the upper or lower joint components and from the disc space. The bridge component has a distal end opposite the one of the either upper or lower joint components. The distal end of the bridge component comprises a connection component adapted to receive a fastener.

In another embodiment, a prosthetic system for implantation between upper and lower vertebrae comprises an upper joint component having an upper contact surface and an upper articulation surface. The system further has a lower joint component comprising a lower contact surface and a lower articulation surface configured to movably engage the upper articulation surface to form an articulating joint. The articulating joint is configured for implantation within a disc space between the upper and lower vertebrae, allowing the upper and lower vertebrae to move relative to one another. The lower joint component further includes a first bumper spaced apart from and disposed anteriorly of the lower articulation surface and adapted to contact the upper joint component to prevent dislocation of the articulating joint.

In another embodiment, a prosthetic system for implantation between upper and lower vertebrae comprises an upper anterior joint component having an upper surface adapted to engage the upper vertebra and an upper articulation surface. The system further includes a lower anterior joint component comprising a lower surface adapted to engage the lower vertebra and a lower articulation surface configured to movably engage the upper articulation surface to form an articulating joint allowing the upper and lower vertebrae to move relative to one another. The articulating joint is disposed within a disc space between the upper and lower vertebrae. The system further includes an upper bridge component extending posteriorly from the upper anterior joint component and posteriorly from the disc space and a lower bridge component extending posteriorly from the lower anterior joint component and posteriorly from the disc space. The system also includes a connection component in one of either the upper or lower bridges adapted to receive a fastener and direct the fastener into the respective upper or lower vertebra.

In still another embodiment, a surgical method comprises removing at least a portion of a natural intervertebral disc from between upper and lower vertebrae to create a disc space and removing a portion of at least one articular process from either the upper or lower vertebrae. The method also includes assembling a joint of a first vertebral arthroplasty device by placing a superior component of the first vertebral arthroplasty device in articulating engagement with an inferior component of the first vertebral arthroplasty device and inserting the joint of the first vertebral arthroplasty device into the disc space. The surgical method further includes positioning a posterior extension of the inferior component outside of the disc space and attaching the posterior extension of the inferior component to the lower vertebra with a bone fastener. A first bumper component at an anterior end of the inferior component limits dislocation of the joint of the first vertebral arthroplasty device.

Additional and alternative features, advantages, uses and embodiments are set forth in or will be apparent from the following description, drawings, and claims.

In some exemplary aspects, the motion preservation prosthetic device disclosed herein may include one or more features disclosed in the following patent applications, incorporated in their entirety herein by reference:

U.S. Utility patent application Ser. No. 11/031,602, filed on Jan. 7, 2005 and entitled "Spinal Arthroplasty Device and Method;"

U.S. Utility patent application Ser. No. 11/031,603, filed on Jan. 7, 2005 and entitled "Dual Articulating Spinal Device and Method;"

U.S. Utility patent application Ser. No. 11/031,780, filed on Jan. 7, 2005 and entitled "Split Spinal Device and Method;"

U.S. Utility patent application Ser. No. 11/031,904, filed on Jan. 7, 2005 and entitled "Interconnected Spinal Device and Method;"

U.S. Utility patent application Ser. No. 11/031,700, filed on Jan. 7, 2005 and entitled "Support Structure Device and Method;"

U.S. Utility patent application Ser. No. 11/031,783, filed on Jan. 7, 2005 and entitled "Mobile Bearing Spinal Device and Method;"

U.S. Utility patent application Ser. No. 11/031,781, filed on Jan. 7, 2005 and entitled "Centrally Articulating Spinal Device and Method;"

U.S. Utility patent application Ser. No. 11/031,903, filed on Jan. 7, 2005 and entitled "Posterior Spinal Device and Method;"

U.S. Utility patent application Ser. No. 11/342,961, filed on Jan. 30, 2006 and entitled "Prosthetic Device for Spinal Joint Reconstruction;"

U.S. Utility patent application Ser. No. 11/343,159, filed on Jan. 30, 2006 and entitled "Posterior Joint Replacement Device;" and U.S. Utility patent application Ser. No. 11/494,311, filed on Jul. 27, 2006 and entitled "Prosthetic Device for Spinal Joint Reconstruction."

BRIEF DESCRIPTION OF THE DRAWINGS

FIG. 18-21 are exploded views of motion preserving prosthetic devices according to other embodiments of the present disclosure.

FIG. 22A is a perspective view of a motion preserving prosthetic device according to another embodiment of the present disclosure.

FIG. 22B is a bottom perspective view of one aspect of the motion preserving prosthetic device of FIG. 22A.

DESCRIPTION

Figure 1:
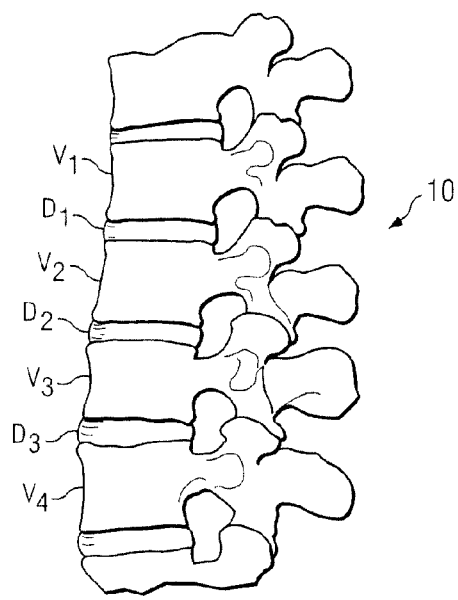
FIG. 1 is a sagittal view of the lumbar spinal region of a healthy, human spinal column

The present disclosure relates generally to systems and methods for spinal surgery and, more particularly in some embodiments, to spinal arthroplasty systems and methods for posterior implantation. For the purposes of promoting an understanding of the principles of the invention, reference will now be made to embodiments or examples illustrated in the drawings, and specific language will be used to describe the same. It will nevertheless be understood that no limitation of the scope of the invention is thereby intended. Any alteration and further modifications in the described embodiments, and any further applications of the principles of the invention as described herein are contemplated as would normally occur to one skilled in the art to which the disclosure relates.

Referring first to FIG. 1, a sagittal view of a vertebral column 10 is shown, illustrating a sequence of vertebrae V1, V2, V3, V4 separated by natural intervertebral discs D1, D2, D3, respectively. Although the illustration generally depicts a lumbar section of a spinal column, it is understood that the devices, systems, and methods of this disclosure may also be applied to all regions of the vertebral column, including thoracic and cervical regions.

Figure 2:
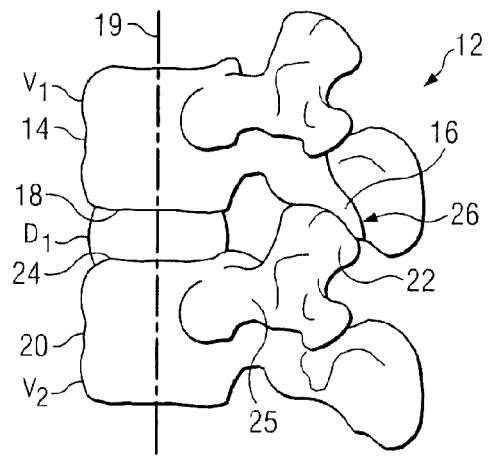
FIG. 2 is a sagittal view of a single spinal joint.
Figure 3:
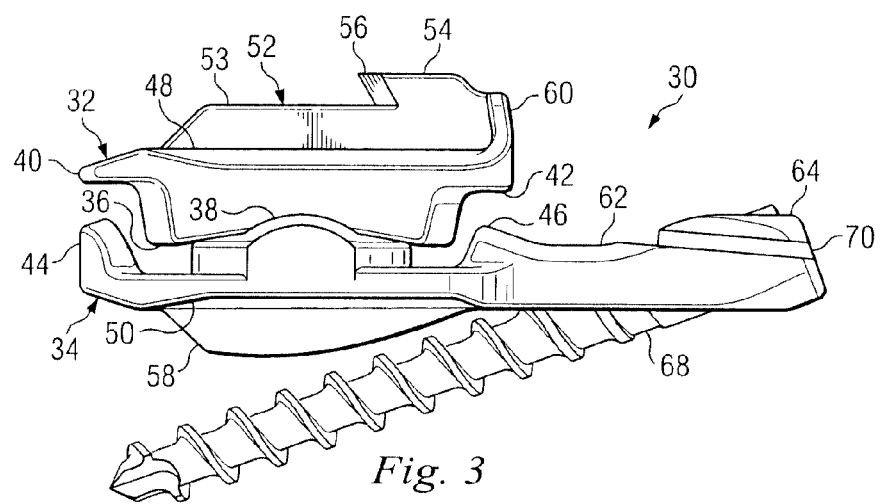
FIG. 3 is lateral view of a motion preserving prosthetic device according to one embodiment of the present disclosure.
Figure 4:
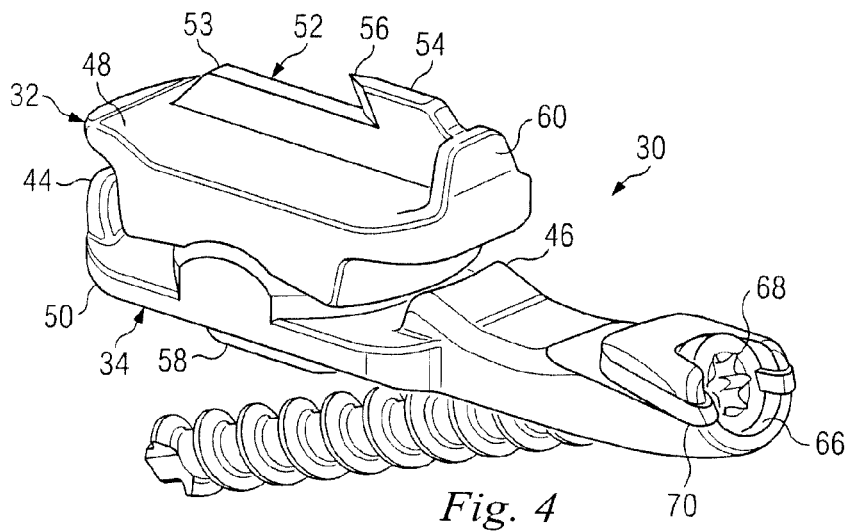
FIG. 4 is a perspective view of the motion preserving prosthetic device of FIG. 3.
Figure 5:
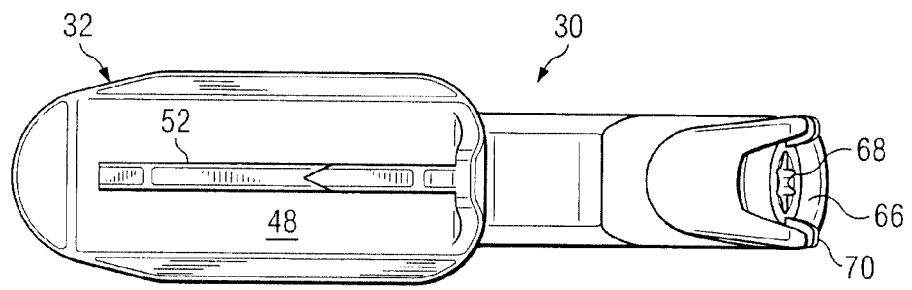
FIG. 5 is a top view of the motion preserving prosthetic device of FIG. 3.
Figure 6:
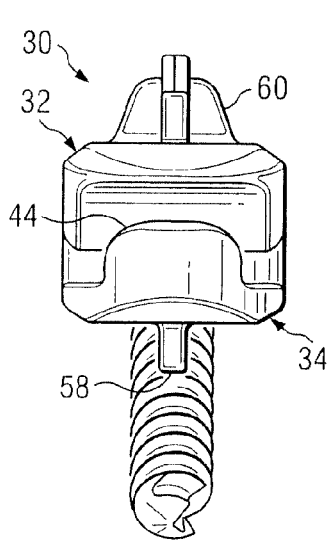
FIG. 6 is an anterior view of the motion preserving prosthetic device of FIG. 3.
Figure 7:
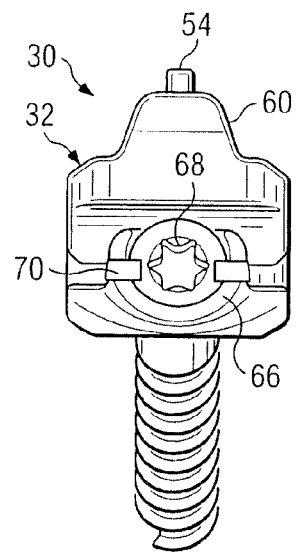
FIG. 7 is a posterior view of the motion preserving prosthetic device of FIG. 3.

Referring now to FIG. 2, a vertebral joint 12 of the vertebral column 10 includes the adjacent vertebrae V1, V2 between which the intervertebral disc D1 extends. The vertebra V1 includes a generally cylindrical vertebral body portion 14, an inferior articular process 16, and an inferior endplate 18. The vertebra V2 includes a generally cylindrical vertebral body portion 20, a superior articular process 22, and a superior endplate 24. For reference purposes, a longitudinal axis 19 extends through the centers of the cylindrical vertebral body portions 14, 20. A pedicle 25 extends between the vertebral body portion 20 and superior articular process 22. The inferior articular process 16 and the superior articular process 22 form a facet or zygapophyseal joint 26. The facet joint 26 has a fluid filled capsule and cartilage to provide articulating surfaces for the articular processes 16, 22. Both the disc D1 and the facet joint 26 permit motion between adjacent bone surfaces, allowing the total vertebral joint 12 a normal range of flexion/extension, lateral bending, and rotational motion. As the disc D1 and/or the facet joint 26 deteriorate due to aging, injury, disease, or other factors, all or portions of the disc, the facet joint, and/or the articular processes 16, 22 may be removed and replaced by a prosthetic device which may preserve motion in the spinal joint 12. Although not described in detail, a second bilateral prosthetic device may also be used to replace a portion of the function of disc D1 and the function of a second facet joint opposite the facet joint 26.

Referring now to FIGS. 3-7, in one embodiment, a prosthetic device 30 may preserve motion in the spinal joint 12. The prosthetic device 30 includes an upper joint component 32 and a lower joint component 34. The upper joint component 32 includes an articulation surface 36 which may be smooth, concave, and generally spherical in shape. The lower joint component 34 includes an articulation surface 38 which may be smooth, convex, and generally spherical in shape. As assembled, the articulation surface 36 may engage the articulation surface 38 to produce a ball-and-socket style anterior joint.

A "spherical" shaped surface is understood to include any curved surface having a uniform radius of curvature and may refer to a spherical cap or a segment of a sphere. In alternative embodiments, non-spherical curved surfaces may function as articulation surfaces to impart specific limits to the range of motion of the prosthetic device. In still another alternative embodiment, the joint may be inverted with the upper articulation surface having a convex shape and the lower articulation surface having a concave articulation surface.

The upper joint component 32 may further include bumpers or motion limiters 40, 42 which in this embodiment are recessed shoulders. The lower joint component 34 includes bumpers or motion limiters 44, 46 which in this embodiment are upwardly protruding extensions, spaced apart from the articulation surface 38. As will be described in greater detail below, the pair of motion limiters 40, 44 and the pair of motion limiters 42, 46 may serve to constrain flexion/extension motion to a desirable range, preventing or limiting the dislocation of the joint formed by the articulation surfaces 36, 38. The motion limiters may be shaped to provide a greater or lesser range of flexion/extension motion. For example, a surface on the motion limiter 44 angled away from the articulation surface 38 may permit greater flexion motion than would a motion limiter surface parallel to the axis 19.

The upper joint component 32 may further include an outer contact surface 48 for interfacing with the vertebral endplate 18, and the lower joint component 34 may include an outer contact surface 50 for interfacing with the vertebral endplate 24.

The upper joint component 32 may further include an upper keel 52 extending from the outer contact surface 48 and comprising an elongated portion 53 and an elongated portion 54. The elongated portion 54 may be taller than the elongated portion 53 to provide the prosthetic device 30 with greater stability in the hard cortical bone of the outer wall of the vertebral body 14. In this embodiment, the raised keel portion 54 has a sharpened and undercut leading edge 56 to encourage aggressive cutting of a channel in the vertebral body 14 and endplate 18 and to help prevent the device 30 from skiving off the vertebral body 14. In this embodiment, the raised keel portion 54 is approximately one-third the length of the upper keel 52 and extends to the posterior edge of the upper joint component to provide additional stability. In alternative embodiments, the upper keel may be longer or shorter to achieve desired stability. The lower joint component 34 may include a lower keel 58 extending from the outer contact surface 50.

In alternative embodiments, the width of the keel may vary. For example, the lower portion of the keel may be narrower than the taller portion of the keel. In other embodiments, the keel may taper or have an undulating wave form. In still another alternative, the keel may be perforated or porous to promote bone ingrowth.

The upper joint component 32 may further include a posterior tab 60 extending upward from the posterior edge of the outer contact surface 48. In this embodiment, the tab 60 may be generally perpendicular or slightly acutely angled relative to the contact surface 48. The tab 60 may be integrally formed with or otherwise abut the posterior end of the upper keel 52. As will be described in greater detail below, the posterior tab 60 may serve as a stop to prevent the device 30 from being inserted too far anteriorly into the intervertebral disc space. The position of the tab 60 may be monitored with fluoroscopy or other visualization methods during surgery to determine the progress of the implantation and to confirm when the device 30 has been completely implanted with the posterior tab 60 in contact with a posterior wall of the vertebral body 14. Because the position of the posterior tab 60 may be fixed relative to a center of rotation of the joint formed by articulation surfaces 36, 38, the location of the posterior tab 60 may serve as an indicator of the location of the center of rotation. After the surgeon has determined the desired location for the center of rotation, the upper joint component 32 may be selected so that as the posterior tab 60 is positioned against the posterior wall of the vertebral body 14, the center of rotation is moved into the desired predetermined location.

The prosthetic device 30 may further include a bridge component 62 extending posteriorly from the lower joint component 34. As installed, the bridge component 62 may further extend posteriorly from the intervertebral disc space between the vertebral bodies 14, 20 and along at least a portion of the pedicle 25 to a distal end 64. In an alternative embodiment, all or a portion of the pedicle 25 may be removed leaving the bridge with little or no support from natural structures.

The distal end 64 of the bridge 62 may include a connection component 66 which in this embodiment is a passage for accepting a fastener 68. In this embodiment, the fastener 68 is a bone screw, however in alternative embodiments, fasteners such as nails, staples, or other mechanical or chemical fasteners may be suitable. The orientation of the connection component 66 permits the fastener 68 to become inserted extrapedicularly such that the screw travels a path obliquely angled or skewed away from a central axis defined through a pedicle. The fastener 68 may be threaded across the a portion of the pedicle 25 and into the vertebral body 20. Extrapedicular fixation may be any fixation into the pedicle that does not follow a path down a central axis defined generally posterior-anterior through the pedicle. In this embodiment, the screw passes through an upper wall of the pedicle and may achieve strong cortical fixation. In all embodiments, the fasteners may be at least partially recessed so as not to interfere with articulations, soft tissues, and neural structures.

As installed, the bridge 62 and the fastener 68 may limit excessive movement of the device 30, particularly during flexion/extension motions. Additionally, the bridge 62 may distribute the loads on the lower vertebra V2, reducing the potential for subsidence of the lower joint component 34 into the vertebral body 20.

The connection component 66 further includes a locking clip 70 which in this embodiment is an elastically deformable C-shaped structure which holds the fastener 68 in place, resisting any backward disengagement of the fastener 68, particularly when the joint 12 is in motion. It is understood that in alternative embodiments, the locking clip may be a cap, a clamp, an adhesive, or other suitable mechanical or chemical systems for limiting movement of the fastener 68.

The size and shape of the joint components 32, 34 and the bridge component 62 may be limited by the constraints of a posterior surgical approach. For example, the anterior joint components 32, 34 may be configured to cover a maximum vertebral endplate area to dissipate loads and reduce subsidence while still fitting through the posterior surgical exposure, Kambin's triangle, and other neural elements. To achieve maximum surface coverage, the material of the anterior joint components 32, 34 may extend anteriorly from the articulation surfaces 36, 38, respectively. The width of the bridge component 62 is also minimized to pass through Kambin's triangle and to co-exist with the neural elements.

In alternative embodiments, the upper and lower joint components may be provided in various heights. For example, the height of the upper component may be increased by manufacturing the component with a thickened contact surface. Likewise, material may be added to increase the overall height of the lower component. Providing the components in a variety of selectable heights may allow the surgeon to create the appropriate tension within the joint to both promote bone growth into the upper and lower components and to achieve a desired range of motion. In still other alternative embodiments, the heights of the upper and lower joint components may increase or decrease along the length of the component to create a desired lordosis or kyphosis. The ability to modify the resulting angle between the upper and lower contact surfaces may allow the surgeon to address variations among patient anatomies or between levels of the vertebral column, such as at the lumbosacral joint (L5-S1). Allowing the surgeon to vary the height, angulation, and performance of the prosthetic device based on the vertebral level or the patient's anatomy may ensure a better fit and a better prognosis for the patient.

The prosthetic device 30 may be formed of any suitable biocompatible material including metals such as cobalt-chromium alloys, titanium alloys, nickel titanium alloys, and/or stainless steel alloys. Ceramic materials such as aluminum oxide or alumnia, zirconium oxide or zirconia, compact of particulate diamond, and/or pyrolytic carbon may also be suitable. Polymer materials may also be used, including any member of the polyaryletherketone (PAEK) family such as polyetheretherketone (PEEK), carbon-reinforced PEEK, or polyetherketoneketone (PEKK); polysulfone; polyetherimide; polyimide; ultra-high molecular weight polyethylene (UHMWPE); and/or cross-linked UHMWPE. The various components comprising the prosthetic device 30 may be formed of different materials thus permitting metal on metal, metal on ceramic, metal on polymer, ceramic on ceramic, ceramic on polymer, or polymer on polymer constructions.

Bone contacting surfaces of the prosthetic device 30 including contact surfaces 48, 50; keels 52, 58; and bridge 62 may include features or coatings which enhance the fixation of the implanted prosthesis. For example, the surfaces may be roughened such as by chemical etching, bead-blasting, sanding, grinding, serrating, and/or diamond-cutting. All or a portion of the bone contacting surfaces of the prosthetic device 30 may also be coated with a biocompatible and osteoconductive material such as hydroxyapatite (HA), tricalcium phosphate (TCP), and/or calcium carbonate to promote bone in growth and fixation. Alternatively, osteoinductive coatings, such as proteins from transforming growth factor (TGF) beta superfamily, or bone-morphogenic proteins, such as BMP2 or BMP7, may be used. Other suitable features may include spikes, ridges, and/or other surface textures.

The prosthetic device 30 may be installed between the vertebrae V1, V2 as will be described below. The prosthetic device 30 may be implanted into a patient using a posterior transforaminal approach similar to the known TLIF (transforaminal lumbar interbody fusion) or PLIF (posterior lumbar interbody fusion) procedures. PLIF style approaches are generally more medial and rely on more retraction of the traversing root and dura to access the vertebral disc space. The space between these structures is known as Kambin's triangle. TLIF approaches are typically more oblique, requiring less retraction of the exiting root, and less epidural bleeding with less retraction of the traversing structures. It is also possible to access the intervertebral space using a far lateral approach, above the position of the exiting nerve root and outside of Kambin's triangle. In some instances it is possible to access the intervertebral space via the far lateral without resecting the facets. Furthermore, a direct lateral approach through the psoas is known. This approach avoids the posterior neural elements completely. Embodiments of the current disclosure may adopt any of these common approaches or combinations thereof.

According to at least one of these approaches, an incision, such as a midline incision, may be made in the patient's back and some or all of the affected disc D1 and surrounding tissue may be removed via the foramina. The superior endplate 24 of the vertebra V2 may be milled, rasped, or otherwise resected to match the profile of the outer contact surface 50 of the lower joint component 34 to normalize stress distributions on the endplate 24, and/or to provide initial fixation prior to bone ingrowth. The preparation of the endplate 24 of vertebra V2 may result in a flattened surface or in surface contours such as pockets, grooves, or other contours that may match corresponding features on the outer contact surface 50. The inferior endplate 18 of the vertebra V1 may be similarly prepared to receive the upper joint component 32 to the extent allowed by the exiting nerve root and the dorsal root ganglia. Depending on whether the facet joint 26 is being replaced, the natural facet joint and the corresponding articular processes 16, 22 may be trimmed to make room for the bridge component 62.

The prosthetic device 30 may then be inserted piecewise through the surgically created opening. That is, components of the prosthetic device 30, including the upper and lower joint components 32, 34 may be fit through the foramina and placed in the intervertebral disc space between the vertebral bodies 14, 20. The pieces of the prosthetic device 30 may be completely separated or two or more of them may be tied or packaged together prior to insertion through the foramina by cloth or other materials known in the art. In cases where at least a portion of the outer annulus of the natural disc can be retained, the lower joint component may be inserted such that it abuts a corresponding portion of the annulus.

The endplates 18, 24 may be milled, chiseled, notched, or otherwise prepared to accept keels 52, 58, respectively. Alternatively, all or portions of the keels may self cut a channel in the endplates. For example, as upper joint component 32 is implanted, the leading elongated portion 52 may follow a pre-cut channel or may itself form the channel as it is driven into the endplate 18. The leading edge 56 may further cut the harder cortical bone of the periphery of the vertebral body 14. Using fluoroscopy or other visualization methods as guidance, the upper joint component 32 may be driven until the posterior tab 60 contacts the posterior wall of the vertebra 14, limiting further insertion. The lower joint component 34 with keel 58 may be driven in a similar manner into the endplate 24 and vertebral body 20. In this embodiment, the upper joint component 32 is held in place, at least initially, by a friction fit. In alternative embodiments, fasteners such as bone screws, staples, adhesives or other mechanical or chemical fasteners may be used to hold the upper joint component in place.

With the upper and lower joint components 32, 34 implanted, the articulation surface 36 may be placed into articulating engagement with the articulation surface 38. The center of rotation of the joint formed by the articulation surfaces 36, 38 may be located posteriorly of the central axis 19 extending longitudinally through the intervertebral disc space between vertebrae V1, V2. Because the posterior tab 60 serves as a stop to prevent over insertion of the upper joint component 32, the final location of the center of rotation may be predetermined by the selection of the upper articulation component.

The bridge 62 may extend posteriorly from the lower joint components 34 and posteriorly from the intervertebral disc space between vertebral bodies 14, 20. The fastener 68 may be inserted through the connection component 66, through a portion of the pedicle 25 and into the vertebral body 20. In this embodiment, the fastener 68 is drilled into the pedicle 25 at an oblique angle relative to the axis of the pedicle and thus is driven into the vertebral body 20 at an angle oblique to the axis 19. The angle of the fastener 68 may serve to limit the fastener from backing out of the bone during later motion of the joint 12. Back out may be further limited by the locking clip 70 which clamps the fastener 68 to the distal end of the bridge 62.

A second prosthetic device, not shown but identical or similar to the prosthetic device 30, may be inserted through a bilaterally opposite TLIF or PLIF type approach in substantially the same manner that has been described above. After insertion, the second prosthetic device may work in concert with the prosthetic device 30 and in a substantially similar manner to provide the range of motion to be described below.

As installed, the anterior ball and socket type joint created by the articulation surfaces 36, 38 may be relatively stable and self-centering. The spherical surfaces of the articulation surfaces permit a full range of motion, including flexion/extension, lateral bending, and rotational motion. Both the anterior joint created by the articulation surfaces 36, 38 and the fastener 68 allow the prosthetic device 30 to resist shear forces, particularly anterior-posterior forces. Movement of the upper joint component 32 relative to the lower joint component 34 may be limited by the displacement of the articulation surface 38 within the articulation surface 36. Rotational motion about the longitudinal axis 19 may be limited by the combined constraint provided by the bilateral pair of prosthetic devices. The keels 52, 58 may further serve to resist shear and rotational motion of the individual components 32, 34.

Figure 8:
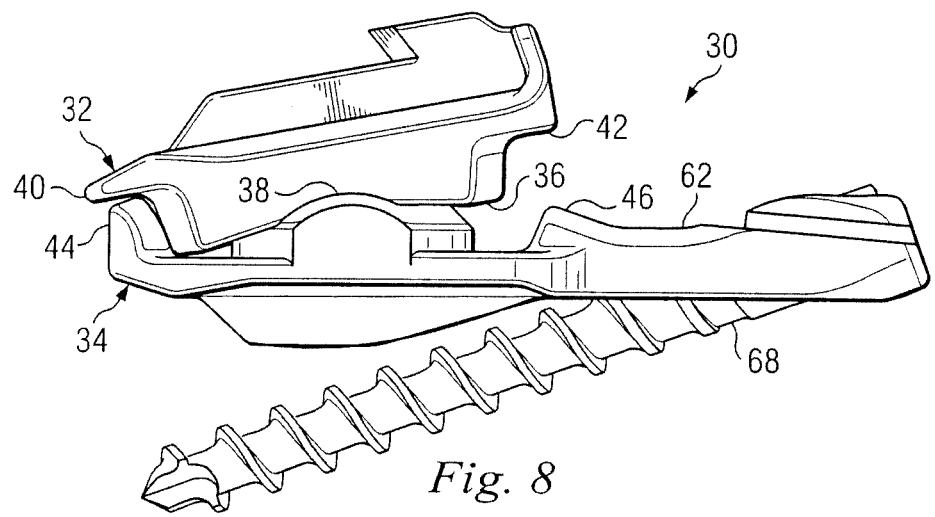
FIG. 8 is a lateral view of the device of FIG. 3 in flexion motion.
Figure 9:
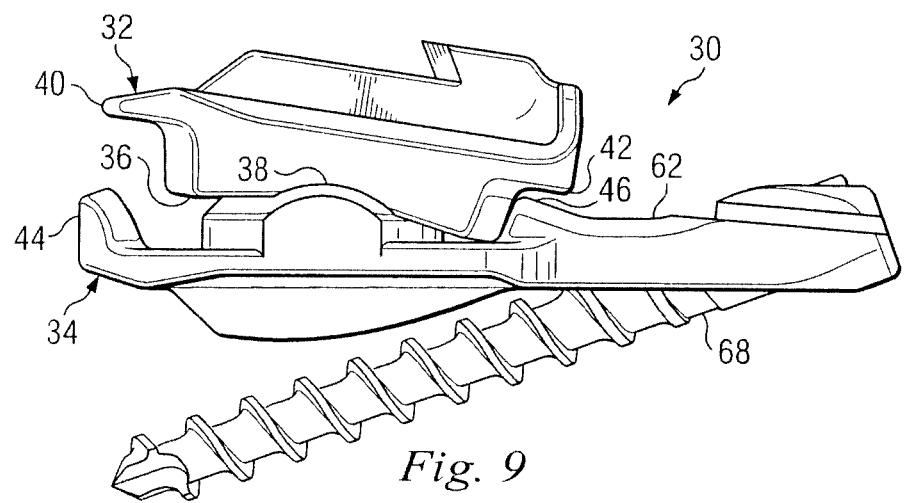
FIG. 9 is a lateral view of the device of FIG. 3 in extension motion.

The function of the facet joint 26 to limit flexion/extension motion in the spinal joint 12 may be restored, at least in part, by the motion limiters 40, 42, 44, 46. For example, as shown in FIG. 8, with the vertebral joint 12 in flexion, the motion limiters 40, 44 may come into contact to prevent further flexion motion and/or to prevent dislocation of the articulation surfaces 36, 38. As shown in FIG. 9, with the vertebral joint 12 in extension, the motion limiters 42, 46 may come into contact to prevent further extension motion and/or to prevent dislocation of the articulation surfaces 36, 38. Flexion/extension motion may be further limited by the bridge 62 held in contact with the pedicle 25 and/or the vertebral body 20 by the fastener 68.

In general, a simple, anteriorly located ball and socket joint which is tightly constrained with each component having the same or similar radii of curvature may allow flexion-extension, lateral bending, and torsion motions while resisting shear forces and limiting translation. Changing the shape of or clearance between the ball and socket components will also permit additional degrees of motion.

Figure 10:
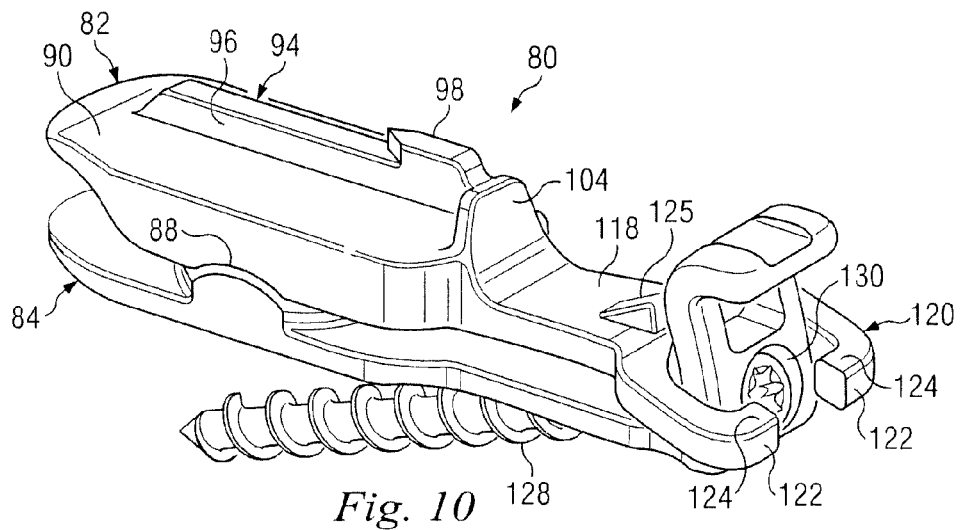
FIG. 10 is a perspective view of a motion preserving prosthetic device according to another embodiment of the present disclosure.
Figure 11:
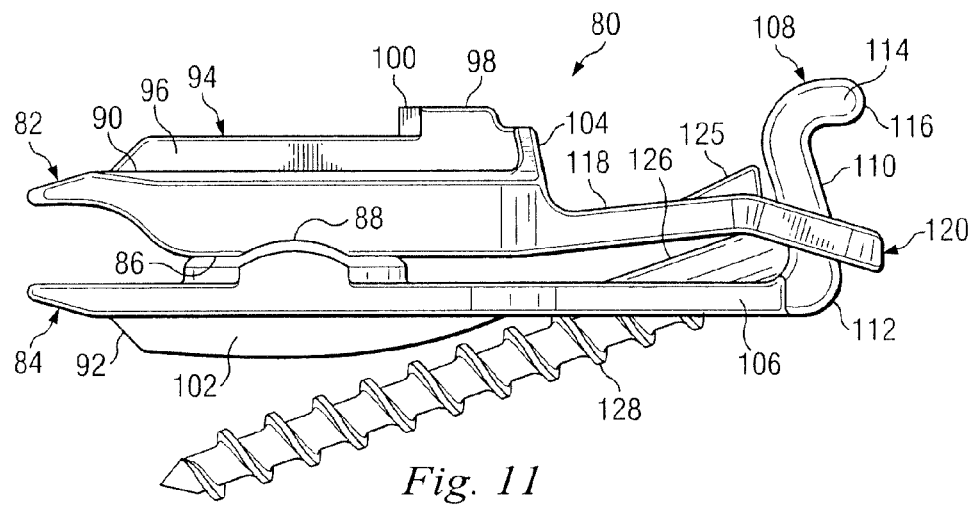
FIG. 11 is a lateral view of the motion preserving prosthetic device of FIG. 10.

Referring now to FIGS. 10 and 11, in this embodiment a prosthetic device 80 may preserve motion in the spinal joint 12. The prosthetic device 80 includes an upper joint component 82 and a lower joint component 84. The upper joint component 82 includes an articulation surface 86 which may be smooth, concave, and generally spherical in shape. The lower joint component 84 includes an articulation surface 88 which may be smooth, convex, and generally spherical in shape. As assembled, the articulation surface 86 may engage the articulation surface 88 to produce a ball-and-socket style anterior joint.

As described above, a "spherical" shaped surface is understood to include any curved surface having a uniform radius of curvature and may refer to a spherical cap or a segment of a sphere. In alternative embodiments, non-spherical curved surfaces may function as articulation surfaces to impart specific limits to the range of motion of the prosthetic device. In still another alternative embodiment, the joint may be inverted with the upper articulation surface having a convex shape and the lower articulation surface having a concave articulation surface.

The upper joint component 82 may further include an outer contact surface 90 for interfacing with the vertebral endplate 18, and the lower joint component 34 may include an outer contact surface 92 for interfacing with the vertebral endplate 24.

The upper joint component 82 may further include an upper keel 94 extending from the outer contact surface 90 and comprising an elongated portion 96 and an elongated portion 98. The elongated portion 98 may be taller than the elongated portion 96 to provide the prosthetic device 80 with greater stability in the hard cortical bone of the outer wall of the vertebral body 14. In this embodiment, the raised keel portion 98 has a sharpened leading edge 100 to cut a channel in the vertebral body 14 and endplate 18 and to help prevent the device 80 from skiving off the vertebral body 14. In this embodiment, the raised keel portion 98 is approximately one-third the length of the upper keel 94 and extends to the posterior edge of the upper joint component 82 to provide additional stability. In alternative embodiments, the upper keel may be longer or shorter. The lower joint component 84 may include a lower keel 102 extending from the outer contact surface 92.

The upper joint component 82 may further include a posterior tab 104 extending upward from the posterior edge of the outer contact surface 90. In this embodiment, the tab 104 may be generally perpendicular or slightly acutely angled relative to the contact surface 90. The tab 104 may be integrally formed with or otherwise abut the posterior end of the upper keel 94. As will be described in greater detail below, the posterior tab 104 may serve as a stop to prevent the device 80 from being inserted too far anteriorly into the intervertebral disc space. The position of the tab 104 may be monitored with fluoroscopy or other visualization methods during surgery to determine the progress of the implantation and to confirm when the device 80 has been completely implanted with the posterior tab 104 in contact with a posterior wall of the vertebral body 14. Because the position of the posterior tab 104 may be fixed relative to a center of rotation of the joint formed by articulation surfaces 86, 88, the location of the posterior tab 104 may serve as an indicator of the location of the center of rotation. After the surgeon has determined the desired location for the center of rotation, the upper joint component 82 may be selected so that as the posterior tab 104 is positioned against the posterior wall of the vertebral body 14, the center of rotation is moved into the desired predetermined location.

The prosthetic device 80 may further include a lower bridge component 106 extending posteriorly from the lower joint component 84. As installed, the lower bridge component 106 may further extend posteriorly from the intervertebral disc space between the vertebral bodies 14, 20 and along at least a portion of the pedicle 25.

In this embodiment, a lower posterior joint component 108 may extend from the lower bridge 106. The posterior joint component 108 may include a post 110 having a bridge end 112 and a tail end 114. The post 110 may be configured to extend generally in a direction along the spinal column.

The bridge end 112 of the post 110 may connect to the lower bridge 106. The post 110 may extend upwardly so that the tail end 114 of the post 60 may be disposed at a location higher than the lower bridge 106. The tail end 114 may include a motion stop 116 configured to limit the range of articulation between the upper and lower joint components 82, 84. In this embodiment, the post 110 may include a straight segment extending between the bridge end 112 and the tail end 114. In one exemplary embodiment, the post 110 may include a curve concentric with the curvature of the articulation surface 88.

The prosthetic device 80 may further include an upper bridge component 118 extending posteriorly from the upper joint component 82. As installed, the upper bridge component 118 may further extend posteriorly from the intervertebral disc space between the vertebral bodies 14, 20. Either of the bridges components 106, 118, but particularly the lower bridge 106, may be a "super" or artificial pedicle which may supplement or replace a natural pedicle.

An upper posterior joint component 120 extends from the upper bridge 118. The upper posterior joint component 120 includes a pair of arms 122 configured to form a C-shape that is adapted to receive the post 110 of the lower posterior joint component 108. A portion of the arms 122 form a motion stop 124 that is configured to cooperate with the motion stop 116 on the post 110. Accordingly, when the upper and lower posterior joint components 108, 120 are assembled as shown in FIGS. 10 and 11, the motion stop 124 and the motion stop 116 cooperate to limit the range of articulation of the prosthetic device 80. The upper bridge component 118 may further include a motion limiter 125 which in this embodiment is a triangular extension that limits anterior motion of the post 110.

A connection component 126, which in this embodiment is an integrally formed tube for accepting a fastener 128, may extend between an opening 130 in the post 110 through the lower bridge component 106. In this embodiment, the fastener 128 is a bone screw, however in alternative embodiments, fasteners such as nails, staples, or other mechanical or chemical fasteners may be suitable. The fastener 128 may be threaded at an oblique angle across the a portion of the pedicle 25 and into the vertebral body 20. As installed, the lower bridge 106 and the fastener 128 may limit excessive movement of the device 80, particularly during flexion/extension motions. Additionally, the lower bridge 106 may distribute the loads on the lower vertebra V2, reducing the potential for subsidence of the lower joint component 84 into the vertebral body 20.

The components of the prosthetic device 80 may be formed of any of the materials listed above for device 30. The prosthetic device 80 may be implanted in a manner similar to that described above for device 30, however in this embodiment, the components may be preassembled before implantation such that the post 110 is inserted through the arms 122 and permitted to translate. As with device 30, the prosthetic device 80 may be paired with a similar or identical bilateral device.

Figure 13:
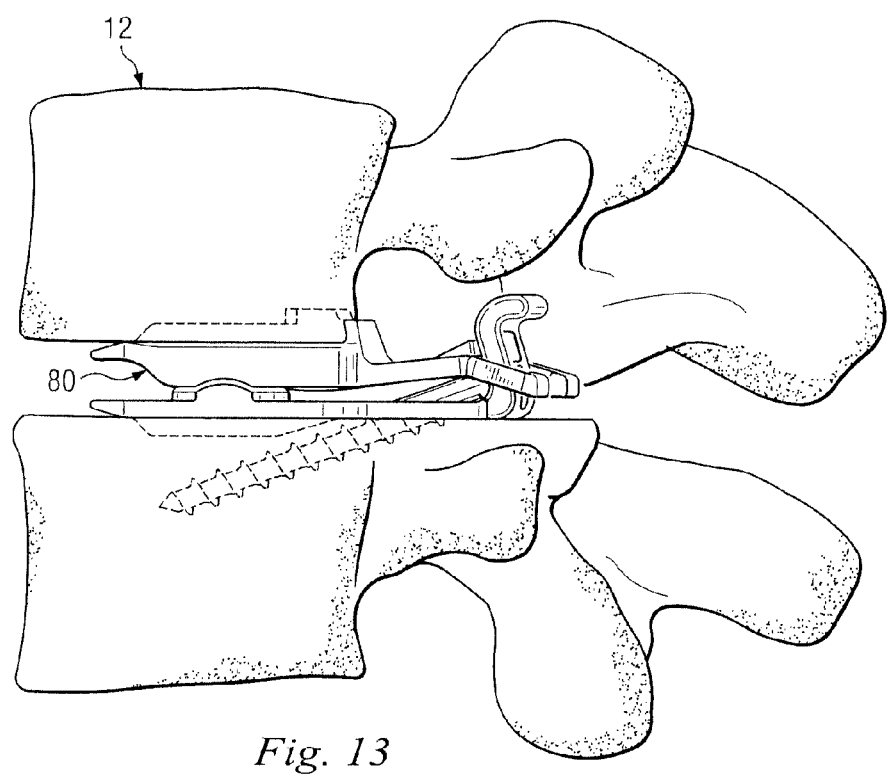
FIG. 13 is a lateral view of the motion preserving prosthetic device of FIG. 10 implanted in a spinal joint.

As installed (FIG. 13), the anterior ball and socket type joint created by the articulation surfaces 86, 88 may be relatively stable and self-centering. The spherical surfaces of the articulation surfaces permit a full range of motion, including flexion/extension, lateral bending, and rotational motion. Together, the anterior joint created by the articulation surfaces 86, 88; the posterior joint created by the upper and lower posterior joint components 108, 120; and the fastener 68 allow the prosthetic device to resist shear forces, particularly anterior-posterior forces. Movement of the upper joint component 32 relative to the lower joint component 34 may be limited by the displacement of the articulation surface 38 within the articulation surface 36 and further by the posterior joint components 108, 120. Rotational motion about the longitudinal axis 19 may be limited by the posterior joint components 108, 120 and the combined constraint provided by the bilateral pair of prosthetic devices. The keels 94, 102 may further serve to resist shear and rotational motion of the individual components 82, 84.

The function of the facet joint 26 to limit flexion/extension motion in the spinal joint 12 may be restored, at least in part, by the posterior joint components 108, 120. For example, when the device 80 is in full flexion, additional flexion and dislocation of the anterior joint may be limited by the cooperation of the motion stop 124 and the motion stop 116. When the device 80 is in full extension, additional extension and dislocation of the anterior joint may be limited by cooperation of the motion limiter 125 with the post 110 and by the cooperation of the upper bridge component 118 with the connection component 126. Flexion/extension motion may be further limited by the lower bridge 106 held in contact with the pedicle 25 and/or the vertebral body 20 by the fastener 128.

Figure 12:
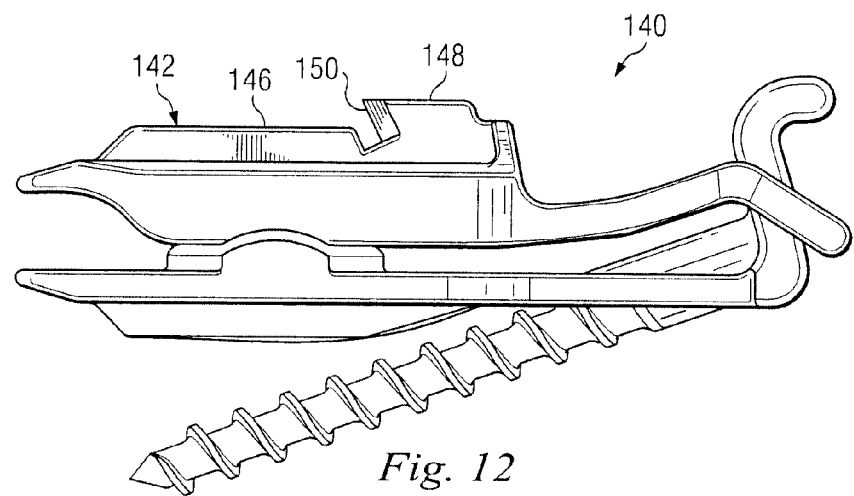
FIG. 12 is a lateral view of a motion preserving prosthetic device according to another embodiment of the present disclosure.

Referring now to FIG. 12, in this embodiment, a prosthetic device 140 may be substantially similar to the prosthetic device 80, however in this embodiment a keel 142 may include an extended portion 146 and an extended portion 148. The extended portion 148 may be taller than the extended portion 146 and may include an undercut portion 150 to permit aggressive cutting of the vertebral body 14 during implantation.

Figure 14:
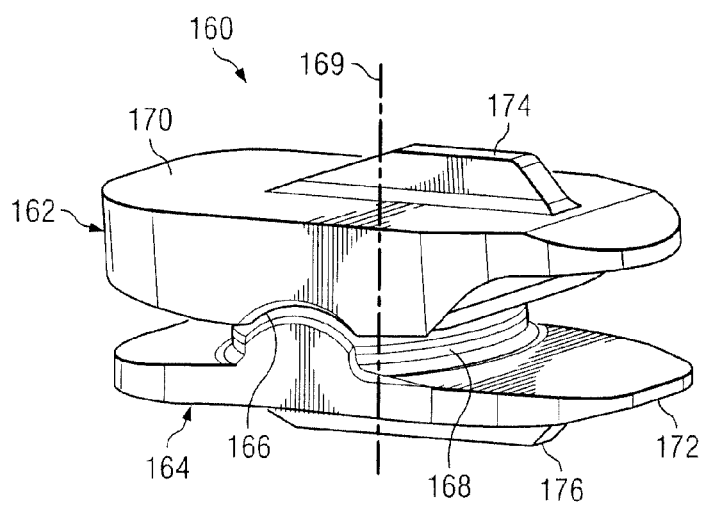
FIG. 14 is a perspective view of a motion preserving prosthetic device according to another embodiment of the present disclosure.

Referring now to FIG. 14, in this embodiment a prosthetic device 160 may preserve motion in the spinal joint 12. The prosthetic device 160 includes an upper joint component 162 and a lower joint component 164. The upper joint component 162 includes an articulation surface 166 which may be smooth, concave, and generally spherical in shape. The lower joint component 164 includes an articulation surface 168 which may be smooth, convex, and generally spherical in shape. As assembled, the articulation surface 166 may engage the articulation surface 168 to produce a ball-and-socket style anterior joint. As shown in this embodiment, the center of rotation of the ball-and-socket style anterior joint is positioned posteriorly of a geometric midline 169. As installed, this posteriorly oriented center of rotation may generate more natural dynamics in the vertebral joint 12.

As described above, a "spherical" shaped surface is understood to include any curved surface having a uniform radius of curvature and may refer to a spherical cap or a segment of a sphere. In alternative embodiments, non-spherical curved surfaces may function as articulation surfaces to impart specific limits to the range of motion of the prosthetic device. In still another alternative embodiment, the joint may be inverted with the upper articulation surface having a convex shape and the lower articulation surface having a concave articulation surface.

The upper joint component 162 may further include an outer contact surface 170 for interfacing with the vertebral endplate 18, and the lower joint component 34 may include an outer contact surface 172 for interfacing with the vertebral endplate 24.

The upper joint component 162 may further include an upper keel 174 extending from the outer contact surface 170. In this embodiment, a greater portion of the keel 174 may extend anteriorly of the midline 169 than extends posteriorly. This anterior orientation of the keel 174 may enhance the purchase of the upper joint component during movement in the joint 12 and may serve to resist otherwise undesirable excessive motion that would be created in the anterior of the device 160 by the posterior orientation of the center of rotation of the ball-and-socket joint. In alternative embodiments, the upper keel may be longer or shorter. The lower joint component 164 may include a lower keel 176 extending from the outer contact surface 172.

The components of the prosthetic device 160 may be formed of any of the materials listed above for device 30. The prosthetic device 160 may be implanted in a manner similar to that described above for device 30, however in this embodiment, the entire device 160 may be positioned within the intervertebral disc space between the vertebral bodies 14, 20. As with device 30, the prosthetic device 80 may be paired with a similar or identical bilateral device.

As installed, the anterior ball and socket type joint created by the articulation surfaces 166, 168 may be relatively stable and self-centering. The spherical surfaces of the articulation surfaces permit a full range of motion, including flexion/extension, lateral bending, and rotational motion. Because this embodiment lacks posterior components substantially extending from the intervertebral disc space, the natural facet joint 26 may be preserved or may be replaced or augmented by other systems known in the art. Rotational motion about the longitudinal axis 19 may be limited by the combined constraint provided by the bilateral pair of prosthetic devices. The keels 174, 176 may further serve to resist shear and rotational motion of the individual components 162, 164.

Figure 15:
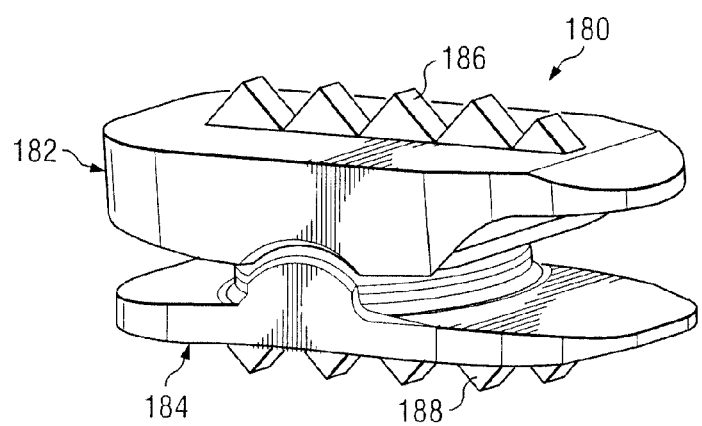
FIG. 15-17 are perspective views of motion preserving prosthetic devices according to other embodiments of the present disclosure.

Referring now to FIG. 15, in this embodiment, a prosthetic device 180 may preserve motion in the spinal joint 12. The prosthetic device 180 includes an upper joint component 182 and a lower joint component 184. The device 180 may be substantially similar to the device 160 with the exception that the upper joint component 182 includes a keel system 186 that includes a series of saw-toothed projections for anchoring into the vertebral endplate 18. A similar keel system 188 extends from the lower joint component 184. The peaks and widths of the saw-tooth projections may be uniform or may vary across the length of the keel system.

Figure 16:
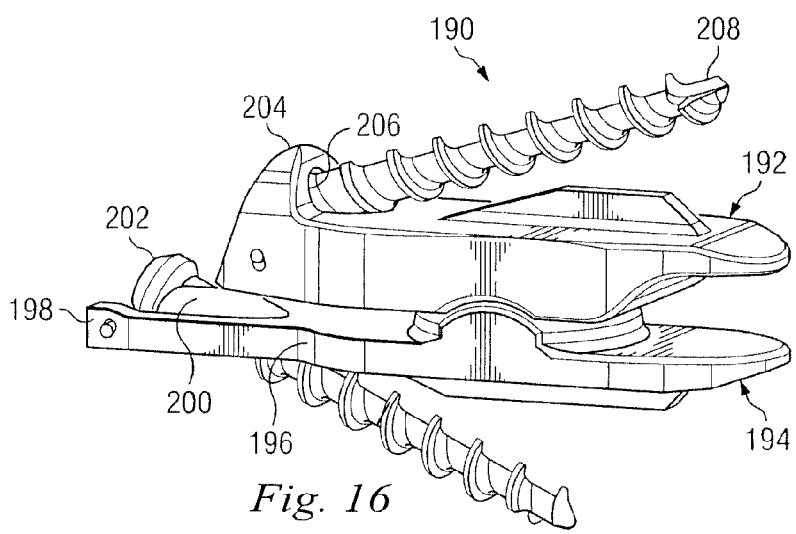

Referring now to FIG. 16, in this embodiment, a prosthetic device 190 may preserve motion in the spinal joint 12. The prosthetic device 190 includes an upper joint component 192 and a lower joint component 194. The device 190 may be substantially similar to the device 160 with the differences to be described below. In this embodiment, the prosthetic device 190 may further include a bridge component 196 extending posteriorly from the lower joint component 194. As installed, the bridge component 196 may further extend posteriorly from the intervertebral disc space between the vertebral bodies 14, 20 and along at least a portion of the pedicle 25 to a distal end 198. In an alternative embodiment, all or a portion of the pedicle 25 may be removed leaving the bridge with little or no support from natural structures.

The distal end 198 of the bridge 196 may include a connection component 200 which in this embodiment is a passage for accepting a fastener 202. In this embodiment, the fastener 202 is a bone screw, however in alternative embodiments, fasteners such as nails, staples, or other mechanical or chemical fasteners may be suitable. The orientation of the connection component 200 permits the fastener 202 to become inserted extrapedicularly such that the screw travels a path obliquely angled or skewed away from a central axis defined through a pedicle. The fastener 202 may be threaded across the a portion of the pedicle 25 and into the vertebral body 20. Extrapedicular fixation may be any fixation into the pedicle that does not follow a path down a central axis defined generally posterior-anterior through the pedicle. In this embodiment, the screw passes through an upper wall of the pedicle and may achieve strong cortical fixation. In all embodiments, the fasteners may be at least partially recessed so as not to interfere with articulations, soft tissues, and neural structures.

As installed, the bridge 196 and the fastener 202 may limit excessive movement of the device 190, particularly during flexion/extension motions. Additionally, the bridge 196 may distribute the loads on the lower vertebra V2, reducing the potential for subsidence of the lower joint component 194 into the vertebral body 20. As described above, the connection component may include a locking clip or other suitable mechanical or chemical systems for limiting movement and disengagement of the fastener 202.

The upper joint component 192 may also include a connection component which, similar to the posterior tab 60 of the device 30, extends generally upward from the upper surface of the upper joint component 192. The connection component 192 includes a through passage 206 sized to receive a fastener 208. The connection component 192 may serve as both an insertion stop as the upper joint component 192 is inserted into the intervertebral disc space and as an entry point for directing the fastener 208 into the vertebral body 14.

As installed, the fastener 208 may limit posterior migration and/or dislocation of the upper joint component 192 and may also limit excessive movement of the device 190, particularly during flexion/extension motion. Locking clips or other blocking devices may be used to prevent the fastener 208 from becoming disengaged. In alternative embodiments the size and shape of the connection component may be varied. For example the connection component may be a U-shaped recess still sized to accept a fastener or may include multiple passages to accept a staple or multiple fasteners.

Figure 17:
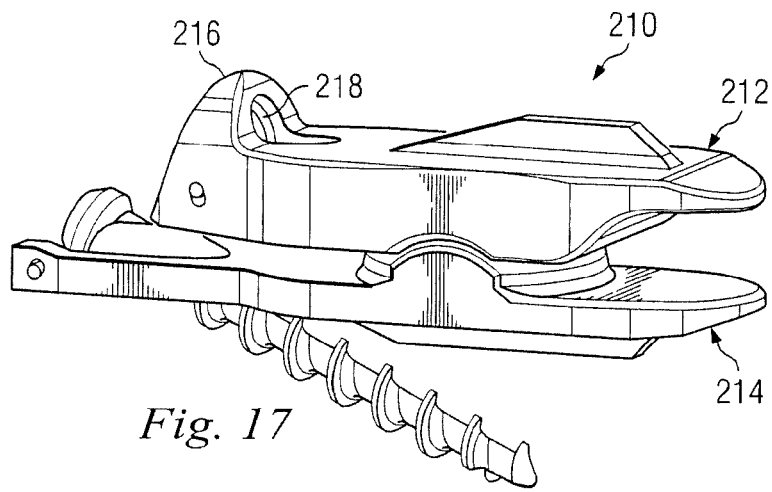

Referring now to FIG. 17, in this embodiment, a prosthetic device 210 may preserve motion in the spinal joint 12. The prosthetic device 210 includes an upper joint component 212 and a lower joint component 214. The device 210 may be substantially similar to the device 190, with the exception that in this embodiment, the upper joint component fastener may be omitted. Like the upper joint component 192, the upper joint component 212 may include a connection component 216 having a through passage 218. In this embodiment, the omission of the upper fastener may serve to eliminate unnecessary constraint in the anterior joint formed by the upper and lower joint components. Further, the passage 218, unoccupied by a fastener, may permit bone ingrowth, allowing the upper joint component 212 to become fixed to the vertebra V1 over time.

Figure 18:
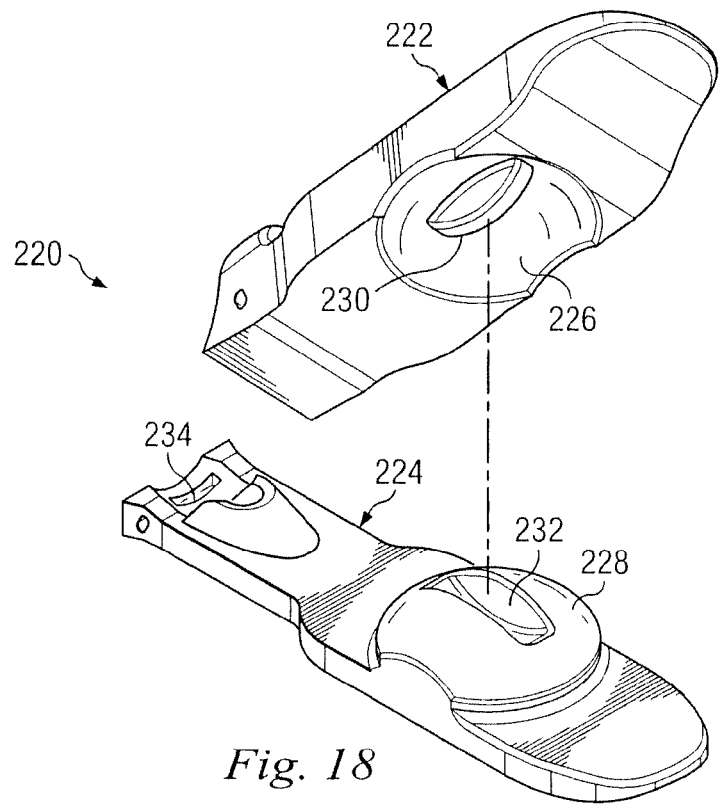

Referring now to FIG. 18, in this embodiment, a prosthetic device 220 may preserve motion in the spinal joint 12. The prosthetic device 220 includes an upper joint component 222 and a lower joint component 224. The device 220 may be substantially similar to the device 190 and may further include features not shown in detail for device 190.

The upper joint component 222 includes an articulation surface 226 which may be smooth, concave, and generally spherical in shape. The lower joint component 224 includes an articulation surface 228 which may be smooth, convex, and generally spherical in shape. As assembled, the articulation surface 226 may engage the articulation surface 228 to produce a ball-and-socket style anterior joint. A projection 230 may extend from the articulation surface 226. In this embodiment the projection 230 is arched or "rocker" shaped with a narrower width in the lateral dimension than the length in the anterior/posterior dimension. A recess or slot 232 may extend into the articulation surface 228. The length of the slot 232 may extend in a generally anterior/posterior direction with the length of the slot being greater than the width of the slot. In this embodiment the base of the slot 232 is curved to generally match the shape of the projection 230. In alternative embodiments, the base of the slot may be flat. The projection 230 is sized to cooperate with the slot 232 to permit flexion/extension motion in the anterior joint while resisting shear forces and torsional motion at the anterior joint.

In alternative embodiments, the projection and the slot may be shaped to permit other types of motion in the anterior joint. For example a slot wider than the projection may permit some torsion or translation between the articulation surfaces. A projection having a more cylindrical-type shape (See FIG. 21) may permit torsional motion with restricting anterior/posterior translation and joint dislocation.

As shown in detail in this embodiment, the lower joint component 224 may further include a restraint slot 234 to receive a locking clip (not shown), as described above for FIG. 3, to prevent a bone fastener from backing out from the bone.

Figure 19:
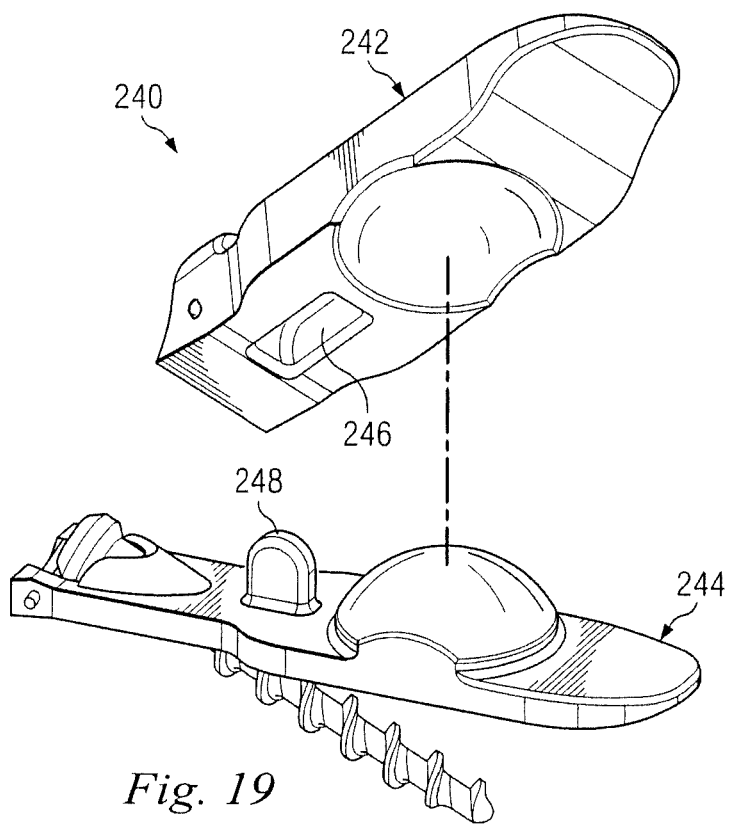

Referring now to FIG. 19, in this embodiment, a prosthetic device 240 may preserve motion in the spinal joint 12. The prosthetic device 240 includes an upper joint component 242 and a lower joint component 244. The device 220 may be substantially similar to the device 190 with differences to be described as follows.

The upper joint component 222 includes a recess 246 which may be arched shaped and located posteriorly of the primary spherical articulation joint. The lower joint component 224 includes an arched shaped projection 248 also located posteriorly of the primary spherical articulation joint and sized to fit within the recess 246. With the device 240 assembled, the projection 248 is inserted inside the recess 246 to resist dislocation and to resist undesirable motion. This configuration serves to resist both anterior/posterior and lateral shear forces and to resist torsion while permitting freedom in flexion/extension motion. Also, the tighter the fit between the projection and the recess, the more lateral bending will be restricted.

Figure 20:
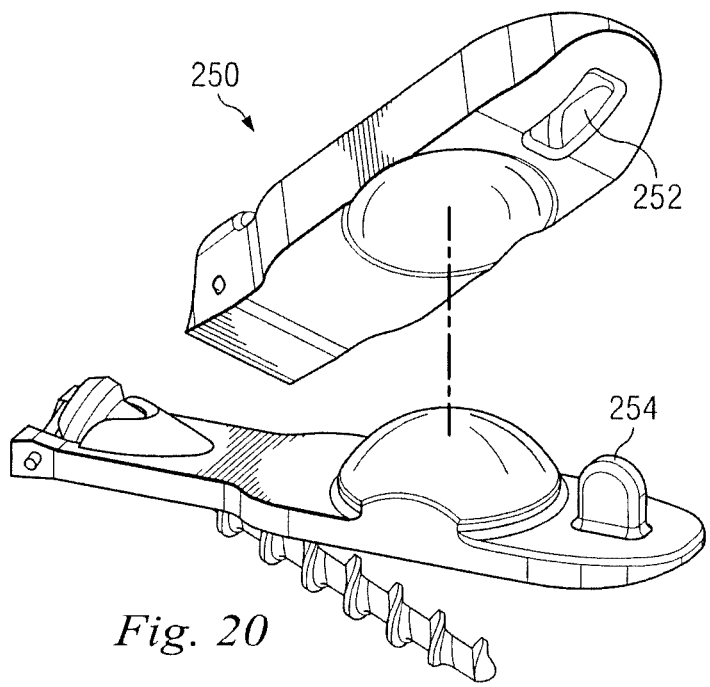

FIG. 20 depicts a device 250 that may be substantially similar to the device 240, however in this embodiment, a projection 254 is inserted into a recess 252, with both the projection and the recess located anteriorly of the primary spherical articulation joint. This configuration serves to resist both anterior/posterior and lateral shear forces and to resist torsion while permitting freedom in flexion/extension motion. Also, the tighter the fit between the projection and the recess, the more lateral bending will be restricted.

Referring now to FIG. 21, a prosthetic device 260 may preserve motion in the spinal joint 12. The prosthetic device 260 includes an upper joint component 262 and a lower joint component 264. The device 260 may be substantially similar to the device 220 however the projection 266 extending from the articulation surface of the upper joint component 262 may be cylindrical and sized to be received into a mating cylindrical opening in the lower articulation surface of the lower joint component 264. This embodiment may resist shear forces and dislocation while permitting torsional motion.

Referring now to FIGS. 22A&B, a prosthetic device 270 may preserve motion in the spinal joint 12. The prosthetic device 270 includes an upper joint component 272 and a lower joint component 274. The device may be substantially similar to the device 240 with the differences to be described. In this embodiment a pair of bumpers 276 extend from the lower joint component 274, one to the anterior side of the articulation joint and another to the posterior side of the articulation joint. The bumpers 276 are generally cylindrical but in alternative embodiments may be spherical, domed shaped or any other suitable shape to provide dampening. A pair of recesses 278 extend into the upper joint component 272. As shown, the recesses may be wider than the bumpers 276 to permit more torsional range of motion and more lateral bending.

As assembled, the bumpers 276 may extend into the respective recesses 278 and serve to dampen or cushion the motion between the upper and lower joint components 272, 274. Although the bumpers may be formed of a rigid material as are the projections 248, 254, in this embodiment, the bumpers are formed of an elastomeric material or any other resilient material that may provide dampening between the joint components, especially during flexion/extension motion. In alternative embodiments, mechanical springs or other mechanical dampeners may be provided between the upper and lower joint components.

Figure 23:
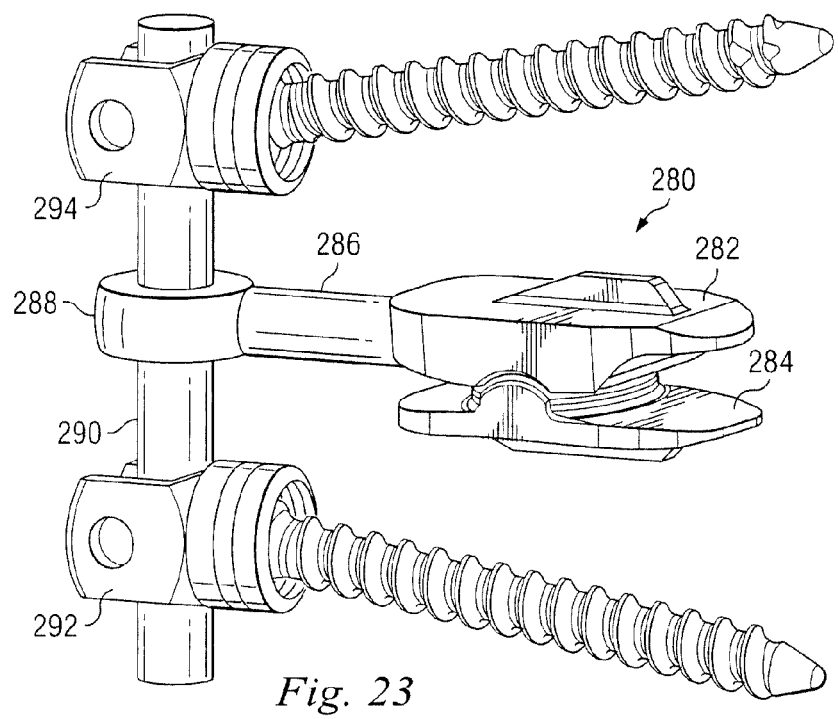
FIGS. 23-25 are perspective views of motion preserving prosthetic devices according to other embodiments of the present disclosure.
Figure 24:
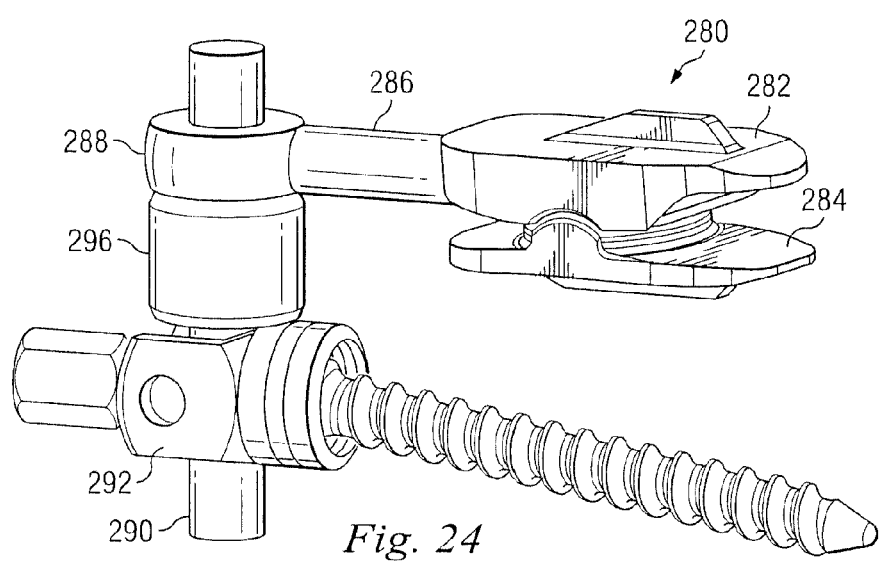

Referring now to FIGS. 23-24, a prosthetic device 280 may preserve motion in the spinal joint 12. The prosthetic device 280 includes an upper joint component 282 and a lower joint component 284. The device 280 may be substantially similar to the device 160 however, in this embodiment, a connection arm 286 extends from the upper joint component 282. The connection arm 286 may be formed of a rigid material such as a metal or a polymer. In alternative embodiments, flexibility in the connection arm may be permitted. The connection arm 286 includes a collar 288 for connection to an elongate rod 290 which may be formed from a rigid material such as titanium or from a more flexible material such as PEEK. In the embodiment of FIG. 23, the rod 290 extends between a pair of polyaxial bone screws 292, 294. Thus, it is understood that the prosthetic device 280 may be used with any rod and screw system known in the art to provide additional constraint at the vertebral joint. As shown in FIG. 24, a spacer 296 may extend between the collar 288 of the connection arm 286. The spacer 296 may serve to maintain a desired distance between the connection arm 286 and the polyaxial screw 292. The spacer 296 may be deformable and resilient such that the collar 288 may compress the spacer under certain types of motion such as flexion/extension. Alternatively the spacer may be relatively rigid, creating a fixed spacing between the collar and the polyaxial screw.

Figure 25:
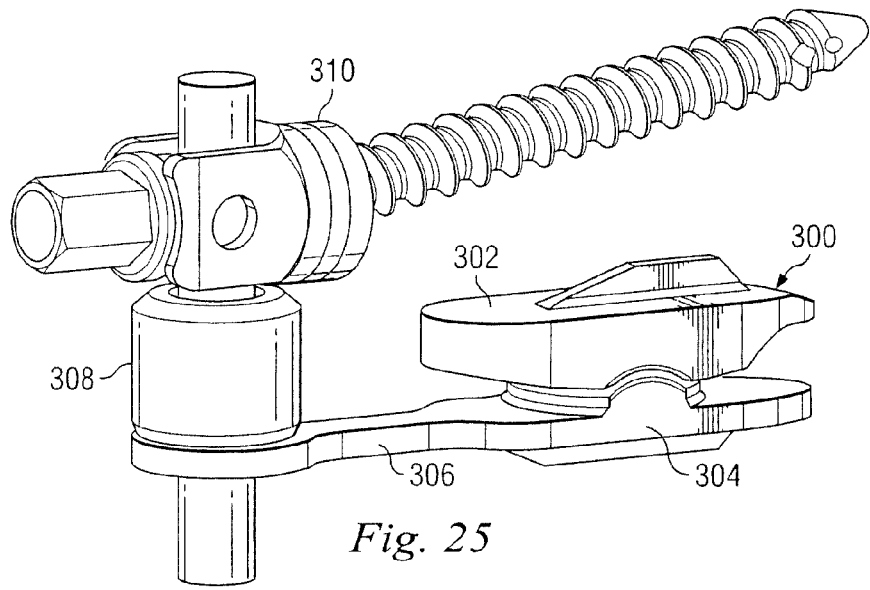

Referring now to FIG. 25, in this embodiment, a prosthetic device 300 may preserve motion in the spinal joint 12. The prosthetic device 300 includes an upper joint component 302 and a lower joint component 304. The device 300 may be substantially similar to the device 280 however in this embodiment, a connection arm 306 extends from the lower joint component 304. In this embodiment, a spacer 308 extends between the connection arm 306 and a polyaxial screw 310.

Figure 26A:
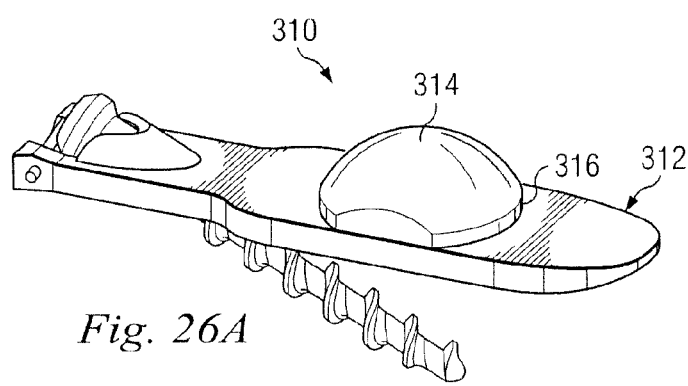
FIG. 26A is a portion of a motion preserving prosthetic device according to another embodiment of the present disclosure.
Figure 26B:
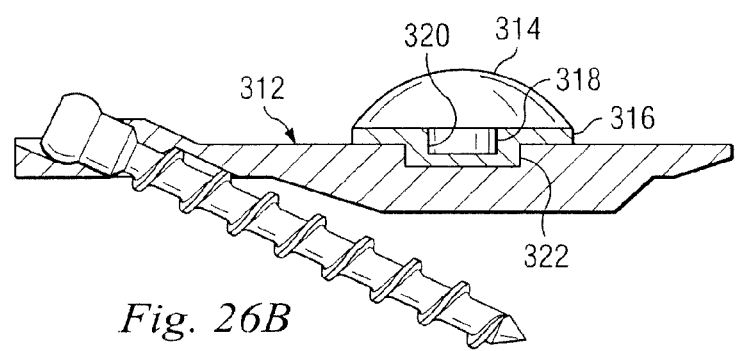
FIG. 26B is a cross sectional view of the motion preserving prosthetic device of FIG. 26A.

Referring now to FIGS. 26A and 26B, in this embodiment, a prosthetic device 310 comprises an upper joint component (not shown) and a lower joint component 312. The device 300 may be substantially similar to the device 190 with the differences to be explained. In this embodiment, a convex lower articulation surface component 314 is separate from the lower joint component 312. A washer 316 extends between the lower articulation surface component 314 and the lower joint component 312 to provide a cushioning effect to the lower articulation surface. In this embodiment, the lower articulation surface component comprises a protrusion 318 that is sized to fit within a recess 320 in the washer 316 to connect the articulation surface component and the washer. The washer 316 is further sized to fit within a recess 322 in the lower joint component 312. The washer may be formed of a resilient and deformable material such as an elastomer to provide a cushioning effect during flexion/extension, lateral bending, and rotation. Alternatively, the material for forming the washer may be relatively rigid and selected for its load bearing and wear-resistant properties. In one embodiment, polyurethane, may be a suitable material. The articulation surface component may be rotatable relative to the washer or may be fixed. Similarly, the washer may be rotatable relative to the lower joint component or may be fixed. The washer 316 permits the articulation surface component 314 to move relative to the lower joint component 312 while providing some constraint on the motion of the articulation surface component. As the resilience of the material of the washer increases, the constraint on the motion of the articulation surface component may decrease.

Figure 27A:
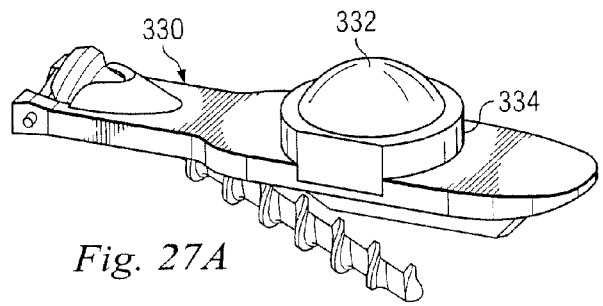
FIG. 27A is a portion of a motion preserving prosthetic device according to another embodiment of the present disclosure.
Figure 27B:
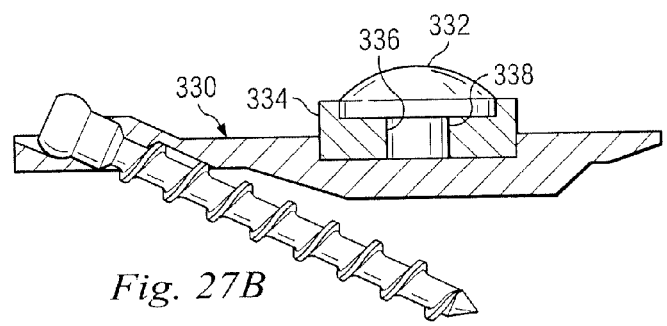
FIG. 27B is a cross sectional view of the motion preserving prosthetic device of FIG. 27A.

Referring now to FIGS. 27A and 27B, in this embodiment a prosthetic device may comprise a lower joint component 330. In this embodiment, an articulation surface component 332 extends through a washer 334 and into contact with the lower joint component 330. The washer 334 comprises an opening 336 to receive and hold a protrusion 338 of the articulation surface component 332. The articulation surface component 332 may be pivotable within the washer and may be cushioned by the washer along an outer periphery. As described above, this washer also provides a cushioning effect to the articulation surface component while constraining some motion of the articulation surface component during flexion/extension, lateral bending, and rotational motion.

Figure 28A:
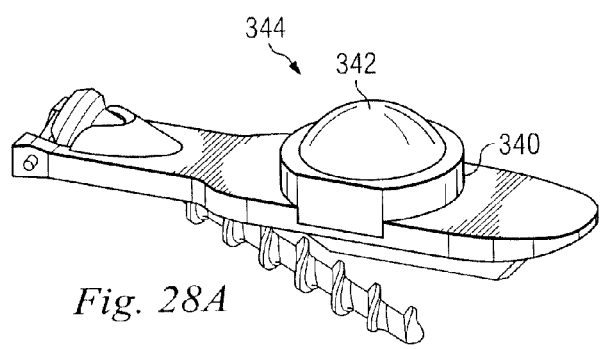
FIG. 28A is a portion of a motion preserving prosthetic device according to another embodiment of the present disclosure.
Figure 28B:
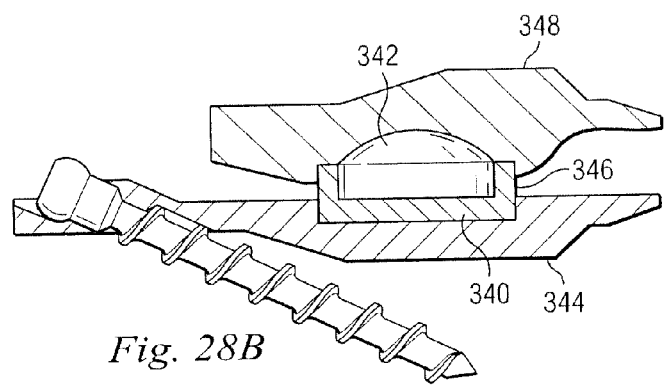
FIG. 28B is a cross sectional view of the motion preserving prosthetic device of FIG. 27A.

Referring now to FIGS. 28A and 28B, in this embodiment a washer 340 extends between an articulation surface component 342 and a lower joint component 344. In this embodiment, the articulation surface component 342 does not contact the lower joint component 344, but rather is completely cushioned by the washer 340. The washer 340 has side walls 346 which extend along the outer periphery of the articulation surface component 342 and which may serve as a bumper between the lower joint component 344 and an upper joint component 348.

The terms "upper" and "lower" are used in some embodiments to describe the position of components of the embodiments. While upper is typically used to describe positions toward the head and lower is used to describe positions toward the tail or foot, as used herein, upper and lower are used simply as modifiers for the relative locations of components of the illustrated embodiments. Components labeled as upper or lower to describe an illustrated embodiment are not intended to limit the orientation of a device or application of a method relative to a patient's anatomy, or to limit the scope of claims to any device or method.

Although the described embodiments generally involve integral formation of the anterior joint components, the bridge and the posterior joint components, it is understood that in alternative embodiments, the components may be modular to accommodate different patient anatomies and to facilitate minimally invasive implantation.

Although only a few exemplary embodiments have been described in detail above, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure. It is understood that all spatial references, such as "horizontal," "vertical," "top," "upper," "lower," "bottom," "left," and "right," are for illustrative purposes only and can be varied within the scope of the disclosure. In the claims, means-plus-function clauses are intended to cover the structures described herein as performing the recited function and not only structural equivalents, but also equivalent structures.

What is claimed is:

1. A surgical method comprising:
   removing at least a portion of a natural intervertebral disc from between upper and lower vertebrae to create a disc space;
   removing a portion of at least one articular process from either the upper or lower vertebrae;
   assembling a joint of a first vertebral arthroplasty device by placing an upper component of the first vertebral arthroplasty device in articulating engagement with a lower component of the first vertebral arthroplasty device;
   inserting the joint of the first vertebral arthroplasty device into the disc space;
   positioning a posterior extension of the lower component outside of the disc space; and
   attaching the posterior extension of the lower component to the lower vertebra with a bone fastener;
   wherein a first bumper component at an anterior end of the lower component limits dislocation of the joint of the first vertebral arthroplasty device.

2. The surgical method of claim 1 further comprising:
   assembling a joint of a second vertebral arthroplasty device; and
   inserting the joint of the second vertebral arthroplasty device into the disc space and in bilateral relationship with the first vertebral arthroplasty device.

3. The surgical method of claim 1 further comprising:
   cutting a channel in at least one of either the upper or lower vertebrae to receive a keel extension of the first vertebral arthroplasty device.

4. The surgical method of claim 3 wherein the cutting is performed by a sharpened leading edge of the keel extension.

5. The surgical method of claim 1 wherein a second bumper component, between the joint of the first vertebral arthroplasty device and the posterior extension, limits dislocation of the joint of the first vertebral arthroplasty device.

6. The surgical method of claim 1 further comprises positioning a tab extending from the superior component of the first vertebral arthroplasty device against a surface of a vertebral body portion of the upper vertebra.

7. The surgical method of claim 6 wherein the step of positioning a tab comprises visualizing the tab engaging the surface of the vertebral body to locate the center of rotation of the joint of the first vertebral arthroplasty device in a predetermined location.

* * * * *